(12) United States Patent
Wu et al.

(10) Patent No.: US 8,246,994 B2
(45) Date of Patent: *Aug. 21, 2012

(54) METHOD FOR DELIVERING AN ACTIVE AGENT USING A HYDROGEL COMPOSITION

(75) Inventors: Daqing Wu, Ithaca, NY (US);
Chih-Chang Chu, Ithaca, NY (US);
Joseph Carozza, Southport, CT (US)

(73) Assignee: Cytogel Pharma, LLC, Darien, CT (US)

( * ) Notice: Subject to any disclaimer, the term of this patent is extended or adjusted under 35 U.S.C. 154(b) by 76 days.

This patent is subject to a terminal disclaimer.

(21) Appl. No.: 12/130,001

(22) Filed: May 30, 2008

(65) Prior Publication Data

US 2008/0226725 A1     Sep. 18, 2008

Related U.S. Application Data

(62) Division of application No. 11/148,641, filed on Jun. 9, 2005.

(60) Provisional application No. 60/578,313, filed on Jun. 10, 2004.

(51) Int. Cl.
*A61K 9/14* (2006.01)

(52) U.S. Cl. .................................................. 424/487

(58) Field of Classification Search ............... 424/487
See application file for complete search history.

(56) References Cited

U.S. PATENT DOCUMENTS

| | | | |
|---|---|---|---|
| 4,663,160 A * | 5/1987 | Tsay et al. ............ | 424/170.1 |
| 5,410,016 A * | 4/1995 | Hubbell et al. .......... | 528/354 |
| 6,107,358 A * | 8/2000 | Harada et al. ........... | 521/133 |
| 6,592,895 B2 | 7/2003 | Lang et al. | |
| 2003/0147835 A1* | 8/2003 | Munro et al. ........... | 424/70.16 |

FOREIGN PATENT DOCUMENTS

WO      WO 00/60956      10/2000

OTHER PUBLICATIONS

Peppas et al (European Journal of Pharmaceutics and Biopharmaceutics 50 (2000) 27-46).*
Border, W.A. et al. "Induction of Mebranous Nephropathy in Rabbits by Administration of an Exogenous Cationic Antigen" *J. Clin. Invest.* Feb. 1982, pp. 451-461, vol. 69.
Cruise, G.M. et al. "Characterization of Permeability and Network Structure of Interfacially Photopolymerized Poly(ethylene glycol) Diacrylate Hydrogels" *Biomaterials*, 1998, pp. 1287-1294, vol. 19.
Lang, M. et al. "Synthesis and Structural Analysis of Functionalized Poly($\epsilon$-Caprolactone)-Based Three-Arm Star Polymers" *J. of Polymer Sci. Part A: Polymer Chemistry*, 2002, pp. 1127-1141, vol. 40, Iss. 8.
Wu, D. et al. "Synthesis, Characterization and Drug Release from Three-Arm Poly($\epsilon$-Caprolactone) Maleic Acid/Poly(ethylene glycol) Diacrylate Hydrogels" *J. Biomater. Sci. Polymer Edn*. 2003, pp. 777-802, vol. 14.
Cho et al., "Clonazepam release from bioerodible hydrogels based on semi-interpenetrating polymer networks composed of poly($\epsilon$-caprolactone) and poly(ethylene glycol) macromer", *International Journal of Pharmaceutics*, 1999, vol. 181, No. 2, pp. 235-242.
Jeong et al., "Thermoreversible gelation of PEG-PLGA-PEG triblock copolymer aqueous solutions", *Macromolecules*, 1999, vol. 32, No. 21, pp. 7064-7069.
Qiu et al., "Miscibility and crystallization of poly(ethylene oxide) and poly($\epsilon$-caprolactone) blends", *Polymer*, 2003, vol. 44, No. 10, pp. 3101-3106.

* cited by examiner

*Primary Examiner* — Benjamin Packard
(74) *Attorney, Agent, or Firm* — Saliwanchik, Lloyd & Eisenschenk

(57) ABSTRACT

New hydrogel, including a hydrogel containing cationic BSA is included in a vaccine to stimulate the immune system to increase the potency of the vaccine.

4 Claims, No Drawings

METHOD FOR DELIVERING AN ACTIVE AGENT USING A HYDROGEL COMPOSITION

CROSS-REFERENCE TO RELATED APPLICATION

This application is a divisional application of co-pending U.S. application Ser. No. 11/148,641, filed Jun. 9, 2005; which claims priority to U.S. Provisional Application Ser. No. 60/578,313, filed Jun. 10, 2004, all of which are hereby incorporated by reference in their entireties, including any figures, tables, or drawings.

TECHNICAL FIELD

This invention is directed at compositions and methods for potentiating vaccines.

BACKGROUND OF THE INVENTION

Hydrogels are known to be useful for delivering drugs and other biologically active agents.

SUMMARY OF THE INVENTION

The subject invention provides new and advantageous hydrogel compositions. In one embodiment, the invention is directed to a delivery system and/or release system comprising a biodegradable hydrogel formed from a hydrogel-forming system comprising a hydrophobic component containing at least one unsaturated group terminal moiety and a hydrophilic component which is polyethylene diacrylate having the formula:

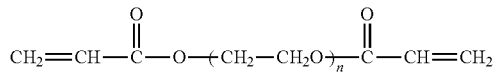

where n is from 8 to 400. The hydrophobic component and hydrophilic component constitute different compounds from one another, and the weight ratio of the hydrophobic component to the weight ratio of the hydrophilic compound is from 1:99 to 99:1. Entrapping or covalently bonded drug (or other biologically active agent to be delivered and/or released) is present in an amount from 0.5 to 5 wt % based on the total weight of polymer precursors.

In a second embodiment, the invention is directed to a vaccine containing the delivery/release system of the first embodiment together with a potentiator to stimulate the immune system to increase the potency of a vaccine. Specifically, one embodiment of the instant invention is directed to a hydrogel comprising bovine serum albumin (BSA) that has been chemically modified to be cationic. In a preferred embodiment, the modified BSA has a pI of greater than 9.5. The invention further concerns the use of the hydrogel in a vaccine with the BSA as a potentiator to stimulate the immune system to increase the potency of a vaccine.

DETAILED DESCRIPTION

In one embodiment, the invention is directed to a delivery system and/or release system comprising a biodegradable hydrogel formed from a hydrogel-forming system comprising a hydrophobic component containing at least one unsaturated group terminal moiety and a hydrophilic component which is polyethylene diacrylate having the formula:

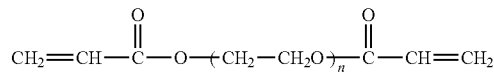

where n is from 8 to 400, where the hydrophobic component and hydrophilic component constitute different compounds from one another, where the weight ratio of said hydrophobic component to the weight ratio of said hydrophilic compound is from 1:99 to 99:1, for example, from 80:20 to 20:80, entrapping or covalently bonded to drug or other biologically active agent to be delivered and/or released, said drug or other biologically active agent being present in an amount from 0.5 to 5 wt % based on the total weight of polymer precursors, said drug or other biologically active agent being bovine serum albumin chemically modified to be cationic.

In a second embodiment, the invention is directed to a vaccine containing the delivery/release system of the first embodiment to stimulate the immune system to increase the potency of the vaccine.

In one embodiment, the instant invention is directed to a hydrogel comprising bovine serum albumin (BSA) that has been chemically modified to enhance the ability to stimulate the immune system. In a preferred embodiment, the modified BSA has been made cationic with modified with a pI of greater than 9.5.

In one embodiment, the hydrophobic component of the hydrogel forming system is a biodegradable polyhydric alcohol ester. Preferably, the polyhydric alcohol ester constituting hydrophobic component of the hydrogel forming system originates from a polyhydric alcohol containing from 3 to 6 hydroxy groups, e.g., glycerol. Preferably, the unsaturated group terminal moiety of the hydrophobic component of the hydrogel forming system is a 2-carboxy ethenyl group, and very preferably, each acyl moiety of the polyhydric alcohol ester constituting hydrophobic component of the hydrogel forming system is poly(ε-caprolactone) where some or each free hydroxyl is functionalized to provide unsaturated group terminal moiety which is 2-carboxy ethenyl group.

The hydrophobic component preferably is polyhydric alcohol ester where some or each of the acyl moieties contain terminal 2-carboxy ethenyl groups and acyl moieties originate from aliphatic homopolymer or copolymer polyesters and contain free hydroxyl at their terminal ends and have weight average molecular weight ranging from 1,000 to 80,000, where some or each of the free hydroxyls are reacted to provide unsaturated terminal moieties which are 2-carboxy ethenyl groups, and alcohol moieties originated from polyhydric alcohol containing from 3 to 6 hydroxyl groups. The hydrophobic component used in working examples herein, denoted PGCL-Ma, has alcohol moiety originating from glycerol and acyl moiety originating from poly(ε-capuolactone) are reacted with maleic anhydride to provide unsaturated terminal moieties which are 2-carboxy ethenyl groups. These polyhydric alcohol esters can be prepared as described in Lang, M. et al. 2002 (*Journal of Polymer Science. Part A: Polymer Chemistry* 40:1127-1141).

In a preferred embodiment, the poly(ethylene glycol) diacrylate hydrophilic component has the formula:

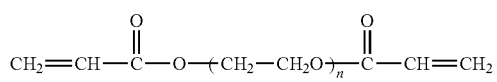

where n is from 8 to 400 e.g., from 40 to 180.

The polyethylene glycols (PEGs) used to produce the poly (ethylene glycol) diacrylate (PEGDA) can be, for example, PEG diol with mass of 2, 3.6 and 8 kDa. The poly(ethylene glycol) diacrylate can be synthesized according to the procedure of Cruise, G. M. et al. 1998 (*Biomaterials* 19:1287) and was synthesized in this way for the PEGDA of the working examples set forth herein.

In the hydrogel forming systems herein, the weight ratio of hydrophobic component to hydrophilic component can range, for example, from 1:99 to 99:1, e.g., from 20:80 to 80:20.

Hydrogels are readily formed from the hydrogel forming systems described herein by dissolving the hydrophobic and hydrophilic precursors in a common solvent, preferably dimethylformamide together with a photoinitiator, e.g., 2,2-dimethoxy 2-phenyl acetophenone (DMPA), e.g., present at 1 to 5% by weight of the precursors, with both precursors together being present preferably at a total concentration of 20 to 40% in solution in the common solvent and then exposing the solution to low-intensity UV irradiation (e.g. 365 nm, 8 W) for 2 to 6 hours to cause photocrosslinking between the molecules of the same and the different precursors.

The hydrogels of the current invention are advantageous compared to those of, for example, U.S. Pat. No. 6,592,895 (incorporated herein by reference) in having a wider range of swelling properties and drug release profiles. When swelling ratio is increased, drug release is hastened (more is released faster). The swelling ratio has been found to increase with increase in ratio of hydrophilic to hydrophobic components and with increase in molecular weight of each of the components. Moreover, the presence of poly(ethylene glycol) in one precursor is advantageous as it is recognized as a very preferred drug carrier by the pharmaceutical industry.

A further aspect of the subject invention is the delivery and/or release of drug or other biologically active agent from a hydrogel carrying such.

The same method for entrapping drug or other biologically active agent can be used as is described in WO 00/60956 published Oct. 19, 2003. In examples herein the drug was added to the precursor solution prior to photocrosslinking to entrap the drug. Typically, the hydrogel contains, for example, a drug loading ranging from 0.5 to 5 wt percent (w/w) based on the total weight of the polymer precursors.

Alternatively, the drug or other biologically active agent can be covalently bonded to one or both of the precursors.

In the working examples herein, bovine serum albumin (BSA) was used to represent the drug or other biologically active agent to evaluate swelling ratio and drug release profile.

The hydrogel forming system can be used to form a delivery system comprising a hydrogel entrapping or covalently bonded to a drug or other biologically active agent to be delivered and/or released. In one embodiment, the hydrogel, along with the biologically active agent can be coated on a vascular stent, e.g., a cardiac stent.

The drugs/biologically active agents for the coatings can be, for example, an anti-inflammation effecting amount for an anti-inflammatory agent, a cholesterol reducing or HDL increase causing amount for an anti-cholesterol agent, a platelet formation inhibiting amount for an antiplatelet agent, a reocclusion ameliorating or preventing amount for agents administered for this purpose, an immune suppression effecting amount to prevent stent rejection and an angiogenesis causing amount for an angiogenesis promoting agent and formation of hydrogel drug/other biologically active agent coating delivery/release system on a stent can be carried out as known in the art. For example, attachment can be directly onto a vascular stent or to a polymer coated vascular stent or as a topcoat on a stent over other biodegradable polymer coating (e.g., poly ester-amide with covalently congregated matrixed drugs).

The term "drug" is used herein to mean a substance for use in the diagnosis, cure, mitigation, treatment or prevention of disease. Typically, drugs have weight average molecular weights ranging from 200 to 1,000. The word "other" in the term "other drugs" is used herein to mean the drug does not contain a group containing the aminoxyl structure.

The term "other biologically active agent" is used herein to include proteins, cytokines, oligo nucleotides including antisense oligo nucleotides, genes, carbohydrates and hormones, but excludes compounds containing an aminoxyl containing radical and "other drug molecule."

The invention is further supported by disclosure and data in Wu, D. et al. 2003 (*J. Biomaterial Sci. Polymer Edn* 14(8): 777-802) which is incorporated herein by reference.

All patents, patent applications, provisional applications, and publications referred to or cited herein are incorporated by reference in their entirety, including all figures and tables, to the extent they are not inconsistent with the explicit teachings of this specification.

The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

Example 1

Preparation of Polyhydric Alcohol Ester

Polyhydric alcohol ester was prepared by ring opening polymerization of ε-caprolactone in the presence of glycerol and reaction of maleic anhydride with some or each of free-hydroxyls at terminal end of acyl moiety of intermediate polyhydric alcohol ester.

The ring opening polymerization of ε-caprolactone in the presence of glycerol was carried out to produce intermediates denoted PGCL-OH-1, PGCL-OH-2 and PGCL-OH-3 as described in Lang, M. et al. 2002 (*Journal of Polymer Science: Part A. Polymer Chemistry* 40:1127-1141) and were respectively converted to PGCL-Ma precursors of 2.4, 5.6 and 13 kDa as follows: PGCL-OH-1, PGCL-OH-2 and PGCL-OH-3 were each placed in a different three-necked flask along with 5 equivalents of maleic anhydride under $N_2$ environment and heated to 130° C. for 1 day.

In each case, processing was then carried out as follows: The reaction mixture was cooled to room temperature and dissolved in chloroform. The chloroform solution was poured into excess petroleum ether to precipitate the product which was denoted PGCL-Ma. The powder precipitate was stirred in 500 ml distilled water for 4 hours for removing any excess maleic anhydride. After filtration, the precipitate was washed with distilled water four times and dried over $P_2O_5$ in vacuum at room temperature until a constant weight was obtained. As indicated above, PGCL-Ma precursors of 2.4, 5.6, and 13 kDa were obtained.

Example 2

Preparation of PEGDA

The preparation of the poly(ethylene glycol) diacrylate precursor denoted PEGDA was carried out as described in Cruise, G. M. et al. 1998 (*Biomaterials* 19:1287). Poly(ethylene glycol) diol starting material of 2, 3.6 and 8 kDa was purchased from Sigma.

To prepare hybrid networks, the PGCL-Ma and PEGDA at composition ratios as described below were dissolved in dimethylformamide to make 40% (w/v) concentration solutions. The PGCL-Ma to PEGDA weight ratios were 100% PGCL-Ma (100:0), 70:30, 50:50, 30:70 and 100% PEGDA (0:100). A photo-initiator, 2,2-dimethoxy 2-phenyl acetophenone (DMPA), 0.1% (w/w) of the precursors, was added to the precursor solution. Resulting solution was homogenous and 2 ml of it was irradiated by a long-wavelength UV lamp (365 nm, 2 W) at room temperature for 3 hours. The remaining solvents in the photocrosslinked networks were evaporated under vacuum at room temperature and dried to constant weight.

Swelling testing was carried out as described by Wu et al. (2003). An initial burst swelling characteristic of hydrophilic polymer networks was found upon immersion in water followed by a gradual swelling phase. The extent of initial increase increased with increase in PEGDA content and the increase in overall swelling ratio increased with increase in PEGDA content.

Bovine serum albumin (BSA) was selected to provide an agent for determination of drug release profile. Testing was carried out as set forth in the paragraph denoted "In vitro BSA release from PGCL-Ma/PEGDA hydrogels" of Wu et al. (2003).

The PGCL-Ma/PEGDA hybrid networks having a high relative PGCL-Ma component presence showed slower release rates and lower amounts of BSA were released than in those hybrid networks having higher relative amount of PEGDA components. The cumulative percentage of released BSA with 1% initial loading concentration was higher than with 2.5% initial loading, in the same hydrogel.

By changing the composition ratio of PGCL-Ma to PEGDA, a wide range of in vitro release profiles were obtained.

Example 3

Modified BSA

We turn now to the component of the delivery/release system, which is native bovine serum albumin, e.g., $M_n$ of 66,000, chemically modified to be cationic, hereinafter cBSA. The cBSA can be made as described in Border, W. A., et al., J. Clin. Invest. 69, 451-461 (February 1982). As described in Border et al, cationization of native bovine serum albumin can be carried out by a modification of the method of Hoare, D. G., et al, J. Biol. Chem. 242, 2447-22453 (1967) using 1-ethyl-3-[(3-dimethylaminopropyl)-carbodiimide hydrochloride] (EDC) and anhydrous ethylenediamine (EDA). In the preparation of Border, the following preparation steps were used: An EDA solution was prepared in a 1-liter glass flask by mixing 67 ml of EDA and 500 ml of distilled water. The pH was adjusted to 4.75 with 350 ml of 5N HCl and the solution was cooled to 25° C. in an ice bath. 5 g of native BSA dissolved in 25 ml of distilled water was added to the EDA solution followed by 1.8 g of EDC. With continuous stirring, the reaction was continued for 120 min maintaining temperature and pH constant and stopped by adding 30 ml of 4M acetate buffer, pH 4.75. The product was dialyzed 48 h against distilled water at 4° C., lyophilized, and stored at 70° C. Border et al measured the pI of the product in thin layers of polyacrylamide gel, pH range 3.5 to 9.5 and the pI was determined to be greater than 9.5.

In a preferred case, the cBSA is entrapped in the hydrogel by dissolving the hydrogel precursors in dimethylformamide to make 40% (w/v) concentration solutions, then adding cBSA at a level of 0.1 to 5% (w/w) of the polymer precursors together with photoinitiator, e.g., 2,2-dimethoxy 2-phenyl acetophenone (0.1% w/w of the precursors) to form a homogenous solution and irradiating e.g., 2 ml, by a long-wavelength UV lamp (365 nm, 2 W) at room temperature for 3 hours.

Example 4

Vaccine Composition

The term "vaccine" is used herein to mean a suspension of whole (live or inactivated) or fractionated bacteria or virus that have been rendered non-pathogenic, given to induce an immune response and prevent disease.

The vaccine can be any of those listed in Table 152-1 at page 1099 of The Merck Manual Seventeenth Edition and in addition vaccines for protection against, for example, smallpox, tuberculosis, usutu, hunta, bear canyon, *rickettsia*, dengue, West Nile, Lyme disease, sis nombre, cyclopspora, *S. aureus* infection, neisseria, *Salmonella* infection, ebola, *listeria, klebsiella*, legionairres' disease, tularemia and *E. coli* infection.

The cBSA delivery release system can admixed with the vaccine for administration therewith, e.g., at a level of 1 to 10% % (w/v) and administered in an amount of 25 to 100 μg/kg.

The inclusion of the cBSA containing release/delivery system in a vaccine stimulates the immune system to increase the potency of the vaccine, i.e., it potentiates the effect of a vaccine compound to the vaccine without the cBSA. This means that the vaccine cane be used at lower strength, e.g., at 1 to 20% of normal concentration and amount, to produce the same protective effect but with reduction of side effects or with the vaccine at full strength to increase proeactive effect.

It should be understood that this example and embodiment described herein are for illustrative purposes only and that various modifications or changes in light thereof will be suggested to persons skilled in the art and are to be included within the spirit and purview of this application.

We claim:

1. A method for delivering a biologically active agent to a desired location in a human or animal, wherein said method comprises administering, to the human or animal, a biodegradable hydrogel comprising a copolymer having a hydrophobic component that is a biodegradable polyhydric alcohol ester containing at least one unsaturated terminal moiety and a hydrophilic component that is poly(ethylene glycol) diacrylate having the formula:

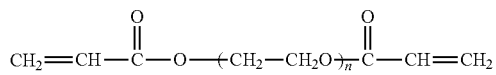

where n is from 8 to 400, wherein the polyhydric alcohol ester originates from a polyhydric alcohol containing from 3 to 6 hydroxy groups, wherein the unsaturated terminal moiety of the hydrophobic component of the hydrogel forming system is a 2-carboxy ethenyl group and wherein said biologically active agent is entrapped in said hydrogel.

2. The method, according to claim 1, wherein said hydrogel has entrapped therein an antigen and a cationic potentiator.

3. The method, according to claim 2, wherein said cationic potentiator has a pI of at least 9.5.

4. The method, according to claim 2, wherein said cationic potentiator is bovine serum albumin (BSA).

* * * * *